United States Patent
Jiang et al.

(10) Patent No.: US 10,533,953 B2
(45) Date of Patent: Jan. 14, 2020

(54) SYSTEM AND METHOD FOR WAFER INSPECTION WITH A NOISE BOUNDARY THRESHOLD

(71) Applicant: KLA-Tencor Corporation, Milpitas, CA (US)

(72) Inventors: Xuguang Jiang, Sunnyvale, CA (US); Yong Zhang, Cupertino, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 195 days.

(21) Appl. No.: 15/388,577

(22) Filed: Dec. 22, 2016

(65) Prior Publication Data

US 2017/0284944 A1 Oct. 5, 2017

Related U.S. Application Data

(60) Provisional application No. 62/317,927, filed on Apr. 4, 2016.

(51) Int. Cl.

| | |
|---|---|
| *G01N 21/00* | (2006.01) |
| *G01N 21/95* | (2006.01) |
| *G06T 7/136* | (2017.01) |
| *G06T 5/40* | (2006.01) |
| *G06T 7/00* | (2017.01) |

(Continued)

(52) U.S. Cl.
CPC .......... *G01N 21/9501* (2013.01); *G06T 5/40* (2013.01); *G06T 7/0002* (2013.01); *G06T 7/0004* (2013.01); *G06T 7/136* (2017.01); *H01L 22/00* (2013.01); *H01L 22/12* (2013.01); *H01L 22/20* (2013.01); *G01N 21/956* (2013.01); *G01N 2021/8883* (2013.01);

(Continued)

(58) Field of Classification Search
CPC ... G01N 2021/8883; G01N 2021/8887; G01N 21/9501; G01N 21/956; G06T 2207/10061; G06T 2207/30148; G06T 5/40; G06T 7/0002; G06T 7/0004; G06T 7/136; H01L 22/00; H01L 22/12; H01L 22/20
USPC .................................................. 356/237.1–6
See application file for complete search history.

(56) References Cited

U.S. PATENT DOCUMENTS

| | | |
|---|---|---|
| 5,805,278 A | 9/1998 | Danko |
| 6,621,570 B1 | 9/2003 | Danko |

(Continued)

OTHER PUBLICATIONS

International Search Report dated Jul. 14, 2017 for PCT/US2017/025528.

*Primary Examiner* — Sunghee Y Gray
(74) *Attorney, Agent, or Firm* — Suiter Swantz pc llo

(57) ABSTRACT

A method includes receiving one or more images of three or more die of a wafer, determining a median intensity value of a set of pixel intensity values acquired from a same location on each of the three or more die, determining a difference intensity value for the set of pixel intensity values by comparing the median intensity value of the set of pixel intensity values to each pixel intensity value, grouping the pixel intensity values into an intensity bin based on the median intensity value of the set of pixel intensity values, generating an initial noise boundary based on a selected difference intensity value in the intensity bin, generating a final noise boundary by adjusting the initial noise boundary, generating a detection boundary by applying a threshold to the final noise boundary, and classifying one or more pixel intensity values outside the detection boundary as a defect.

24 Claims, 11 Drawing Sheets

(51) Int. Cl.
    *H01L 21/66*     (2006.01)
    *G01N 21/956*     (2006.01)
    *G01N 21/88*     (2006.01)

(52) U.S. Cl.
    CPC ........ *G01N 2021/8887* (2013.01); *G06T 2207/10061* (2013.01); *G06T 2207/30148* (2013.01)

(56) References Cited

U.S. PATENT DOCUMENTS

| | | |
|---|---|---|
| 7,092,082 B1 | 8/2006 | Dardzinski |
| 8,664,594 B1 | 3/2014 | Jiang et al. |
| 8,692,204 B2 | 4/2014 | Kojima et al. |
| 8,698,093 B1 | 4/2014 | Gubbens et al. |
| 2006/0193531 A1 | 8/2006 | Roberts et al. |
| 2007/0105245 A1 | 5/2007 | Funakoshi et al. |
| 2009/0299681 A1 | 12/2009 | Chen et al. |
| 2014/0358480 A1 | 12/2014 | Raquel et al. |
| 2015/0048741 A1 | 2/2015 | Shortt et al. |
| 2015/0221076 A1 | 8/2015 | Gao et al. |
| 2015/0333471 A1 | 11/2015 | Chimmalgi et al. |
| 2015/0357179 A1 | 12/2015 | Wilson et al. |
| 2018/0109811 A1* | 4/2018 | Mukherjee ............ H04N 19/65 |
| 2018/0204048 A1* | 7/2018 | Chefd'hotel ......... G06K 9/0014 |
| 2018/0306768 A1* | 10/2018 | Little ................ G01N 21/6456 |

\* cited by examiner

SYSTEM AND METHOD FOR WAFER INSPECTION WITH A NOISE BOUNDARY THRESHOLD

CROSS-REFERENCE TO RELATED APPLICATIONS

The present application claims priority under 35 U.S.C. § 119(e) to U.S. Provisional Patent Application Ser. No. 62/317,927, filed Apr. 4, 2016, titled NOISE BOUNDARY THRESHOLDING (NBT) ALGORITHM FOR LS PLATFORM DEFECT DETECTION, naming Xuguang Jiang and Yong Zhang as inventors, which is incorporated herein by reference in the entirety.

TECHNICAL FIELD

The present invention generally relates to wafer inspection and review, and more particularly, to the generation and implementation of a noise boundary threshold (NBT) procedure during wafer inspection and review.

BACKGROUND

Fabricating semiconductor devices such as logic and memory devices typically includes processing a substrate such as a semiconductor wafer using a large number of semiconductor fabrication procedures to form various features and multiple levels of the semiconductor devices. Multiple semiconductor devices may be fabricated in an arrangement on a single semiconductor wafer and then separated into individual semiconductor devices.

Semiconductor devices may develop defects during the fabrication procedures. Inspection procedures are performed at various steps during a semiconductor manufacturing process to detect defects on a specimen. Inspection procedures are an important part of fabricating semiconductor devices such as integrated circuits, becoming even more important to successfully manufacture acceptable semiconductor devices as the dimensions of semiconductor devices decrease. For instance, detection of defects has become highly desirable as the dimensions of semiconductor devices decrease, as even relatively small defects may cause unwanted aberrations in the semiconductor devices.

One method of defect detection includes checking one or more patterns of review (POR) with one or more procedures, including the Hierarchical and Local Automatic Thresholding (HLAT) and Fast Adaptive Segmented Thresholding (FAST) procedures. The HLAT procedure is highly sensitive and includes multiple non-default (i.e., tunable) operation parameters (e.g., system noise, wafer noise, pattern noise, and the like). As a result, the HLAT procedure is difficult to tune, and is user-dependent.

In contrast, the FAST procedure includes only a single non-default (i.e., tunable) operation parameter and so is quickly tuned, but is of lower sensitivity than the HLAT procedure. Additionally, the FAST procedure may include a sensitivity gap as opposed to the HLAT procedure or a broadband plasma (BBP) inspection system.

Both the HLAT and FAST procedures require a number of ideal-scenario assumptions to be made about the one or more wafers being inspected. For example, both the HLAT and FAST procedures assume that the noise distribution in one or more dies of the one or more wafers is the same. By way of another example, both the HLAT and FAST procedures use a common noise threshold parameter for the one or more dies. By way of another example, both the HLAT and FAST procedure use a common noise threshold parameter for both bright noise and dark noise defects. It is noted herein that both the HLAT and FAST include a dark defect factor for both algorithms to detune dark defects; however, the dark defect factor cannot detect dark defects if the factor is below a bright noise threshold. Real-world scenarios, however, may include uneven noise distributions, uneven bright noise distributions, and/or uneven dark noise distributions. For example, dies adjacent to a particular die on a wafer may include color variation. By way of another example, the one or more dies may have one or more weak signal defects buried underneath one or more stronger signal defects. By way of another example, the one or more dies may be dominated by bright noise and/or dark noise.

The FAST procedure requires an additional ideal-scenario assumption that bright noise and dark noise follow a Gaussian distribution (e.g., Gaussian mean and standard deviation distribution levels) scheme in all three die. Real-world scenarios, however, may include color variation in the adjacent dies to a particular die that prevents bright noise and dark noise from following Gaussian distribution curves.

As such, applying ideal-scenario assumptions to real-world scenarios often results in missing defects of interest (DOI) and a high nuisance rate during wafer inspection and review. Therefore, it would be desirable to provide a system and method that cures the shortcomings of the previous approaches as identified above.

SUMMARY

A wafer inspection system is disclosed, in accordance with one or more embodiments of the present disclosure. In one illustrative embodiment, the system includes an inspection sub-system. In another illustrative embodiment, the system includes a stage configured to secure a wafer. In another illustrative embodiment, the system includes a controller communicatively coupled to the inspection sub-system. In another illustrative embodiment, the controller includes one or more processors configured to execute a set of program instructions stored in memory. In another illustrative embodiment, the program instructions are configured to cause the one or more processors to receive one or more images of three or more die of the wafer from the inspection sub-system. In another illustrative embodiment, the program instructions are configured to cause the one or more processors to determine a median intensity value of a set of pixel intensity values acquired from a same location on each of the three or more die. In another illustrative embodiment, the program instructions are configured to cause the one or more processors to determine a difference intensity value for the set of pixel intensity values by comparing the median intensity value of the set of pixel intensity values to each pixel intensity value. In another illustrative embodiment, the program instructions are configured to cause the one or more processors to group the pixel intensity values into an intensity bin based on the median intensity value of the set of pixel intensity values. In another illustrative embodiment, the program instructions are configured to cause the one or more processors to generate an initial noise boundary based on a selected difference intensity value in the intensity bin. In another illustrative embodiment, the program instructions are configured to cause the one or more processors to generate a final noise boundary by adjusting the initial noise boundary. In another illustrative embodiment, the program instructions are configured to cause the one or more processors to generate a detection boundary by applying a threshold to the final noise boundary. In another illustrative embodiment, the program instructions are configured to cause the one or more processors to classify one or more pixel intensity values outside the detection boundary as a defect.

A method is disclosed, in accordance with one or more embodiments of the present disclosure. In one illustrative embodiment, the method includes receiving one or more images of three or more die of the wafer from an inspection sub-system. In another illustrative embodiment, the method includes determining a median intensity value of a set of pixel intensity values acquired from a same location on each of the three or more die. In another illustrative embodiment, the method includes determining a difference intensity value for the set of pixel intensity values by comparing the median intensity value of the set of pixel intensity values to each pixel intensity value. In another illustrative embodiment, the method includes grouping the pixel intensity values into an intensity bin based on the median intensity value of the set of pixel intensity values. In another illustrative embodiment, the method includes generating an initial noise boundary based on a selected difference intensity value in the intensity bin. In another illustrative embodiment, the method includes generating a final noise boundary by adjusting the initial noise boundary. In another illustrative embodiment, the method includes generating a detection boundary by applying a threshold to the final noise boundary. In another illustrative embodiment, the method includes classifying one or more pixel intensity values outside the detection boundary as a defect.

It is to be understood that both the foregoing general description and the following detailed description are exemplary and explanatory only and are not necessarily restrictive of the present disclosure. The accompanying drawings, which are incorporated in and constitute a part of the characteristic, illustrate subject matter of the disclosure. Together, the descriptions and the drawings serve to explain the principles of the disclosure.

BRIEF DESCRIPTION OF THE DRAWINGS

The numerous advantages of the disclosure may be better understood by those skilled in the art by reference to the accompanying figures in which.

DETAILED DESCRIPTION OF THE INVENTION

Reference will now be made in detail to the subject matter disclosed, which is illustrated in the accompanying drawings.

Referring to FIGS. 1 through 5C, systems and methods for generating and implementing a noise boundary threshold procedure during wafer inspection and review are disclosed, in accordance with one or more embodiments of the present disclosure.

Embodiments of the present disclosure are directed to providing a wafer inspection procedure with improved defect detection capabilities. Embodiments of the present disclosure are also directed to making one or more operational assumptions that more closely resemble real-world scenarios that may occur during wafer inspection and review. Embodiments of the present disclosure are also directed to detecting one or more types of defects on wafers that may be missed by known laser-scanning defect detection procedures, including the HLAT and FAST procedures.

Embodiments of the present disclosure are also directed to generating one or more noise boundaries for the wafer inspection data. Embodiments of the present disclosure are also directed to adjusting the one or more noise boundaries to be adaptive to noise. Embodiments of the present disclosure are also directed to applying a threshold to the adjusted one or more noise boundaries to generate a threshold boundary to separate inspection system noise from one or more true defects.

Advantages of one or more embodiments of the present disclosure include improved defect detection sensitivity. Advantages of one or more embodiments of the present disclosure also include an increased adaptability to various types of wafer inspection system noise. For example, advantages of one or more embodiments of the present disclosure also include detecting one or more weak signal defects. By way of another example, advantages of one or more embodiments of the present disclosure also include detecting color variation among adjacent dies. By way of another example, advantages of one or more embodiments of the present disclosure also include improved defect detection in inspection images dominated by bright and/or dark noise. Advantages of one or more embodiments of the present disclosure also include providing a procedure with only a minimal number of operational parameters are required to be tuned, allowing for a more widespread application of the present disclosure. Advantages of one or more embodiments of the present disclosure also include compatibility with other wafer inspection procedures. Advantages of one or more embodiments of the present disclosure also include increased through-put during wafer inspection by lowering computational requirements.

Figure 1:
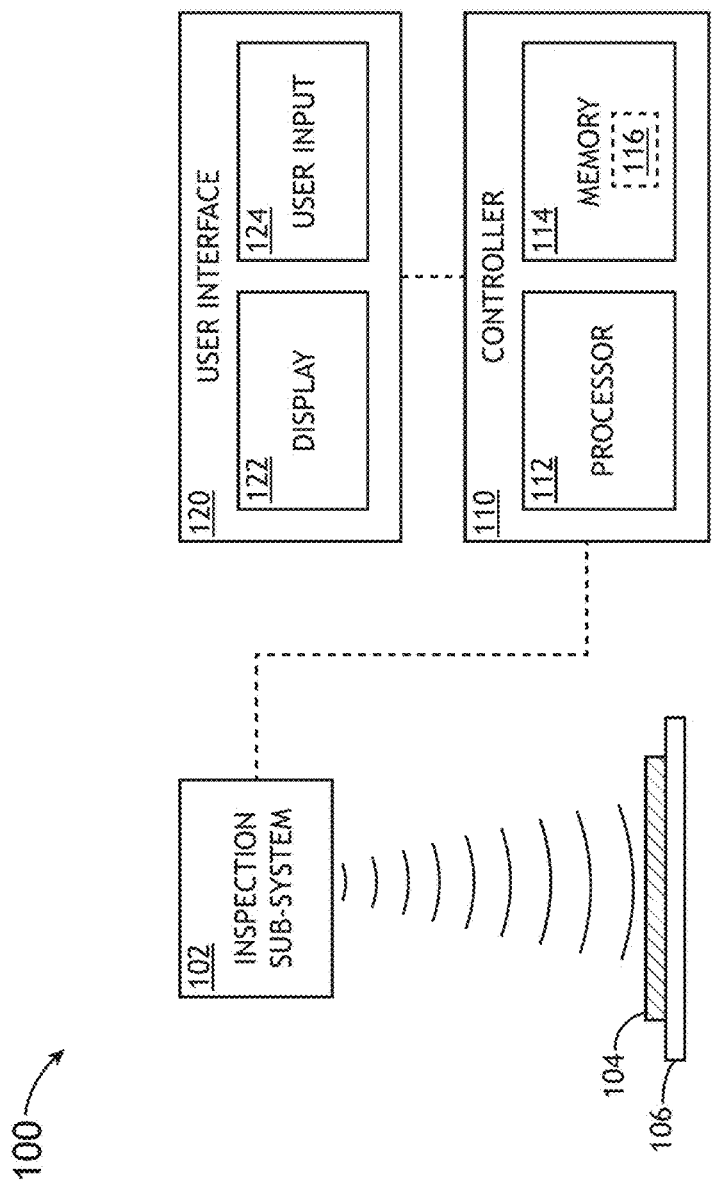
FIG. 1 illustrates a block diagram view of a system for imaging a sample, in accordance with one or more embodiments of the present disclosure.

FIG. 1 illustrates a block diagram view of system 100 for sample inspection, in accordance with one or more embodiments of the present disclosure. In one embodiment, the system 100 includes an inspection sub-system 102. In another embodiment, the system 100 includes a sample stage 106 for securing one or more samples 104. In another embodiment, the system 100 includes a controller 110. In another embodiment, the system 100 includes a user interface 120.

In another embodiment, the inspection sub-system 102 is configured to detect one or more defects of the sample 104. For example, the inspection sub-system 102 may include any appropriate characterization tool known in the art such as, but not limited to, an inspection sub-system or review tool. For example, the inspection sub-system 102 may include, but is not limited to, an optical inspection sub-system. For instance, the optical inspection sub-system may include a broadband inspection sub-system including, but not limited to, a laser sustained plasma (LSP) based inspection sub-system. Additionally, the optical inspection sub-system may include a narrowband inspection sub-system, such as, but not limited to, a laser scanning inspection sub-system. Further, the optical inspection sub-system may include, but is not limited to, a brightfield imaging tool, or a darkfield imaging tool. It is noted herein that the inspection sub-system 102 may include any optical system configured to collect and analyze illumination reflected, scattered, diffracted, and/or radiated from a surface of a sample 104. By way of another example, the inspection sub-system 102 may include, but is not limited to, an electron beam inspection or review tool (e.g., a scanning electron microscopy (SEM) system).

Examples of inspection sub-systems are described in U.S. Pat. No. 7,092,082, issued on Aug. 15, 2006; U.S. Pat. No. 6,621,570 issued on Sep. 16, 2003; and U.S. Pat. No. 5,805,278 issued on Sep. 8, 1998, which are each herein incorporated by reference in the entirety. Example of inspection sub-systems are also described in U.S. Pat. No. 8,664,594, issued on Mar. 4, 2014; U.S. Pat. No. 8,692,204, issued on Apr. 8, 2014; U.S. Pat. No. 8,698,093, issued on Apr. 15, 2014; U.S. Pat. No. 8,716,662, issued on May 6, 2014; U.S. patent application Ser. No. 14/699,781, filed on Apr. 29, 2015; U.S. patent application Ser. No. 14/667,235, filed on Mar. 24, 2015; and U.S. patent application Ser. No. 14/459,155, filed on Aug. 13, 2014, which are each herein incorporated by reference in the entirety.

For purposes of the present disclosure, a defect may be classified as a void, short, particle, residue, scum, or any other defect known in the art.

In another embodiment, although not shown, the inspection sub-system 102 may include an illumination source, a detector and various optical components for performing inspection (e.g., lenses, beam splitters and the like). For example, the inspection sub-system 102 may include any illumination source known in the art. For instance, the illumination source may include, but is not limited to, a broadband light source or a narrowband light source. In addition, the illumination source may be configured to direct light to a surface of the sample 104 (via various optical components) disposed on the sample stage 106. Further, the various optical components of the inspection sub-system 102 may be configured to direct light reflected and/or scattered from the surface of the sample 104 to the detector of the inspection sub-system 102. By way of another example, the detector of the inspection sub-system 102 may include any appropriate detector known in the art. For instance, the detector may include, but is not limited to, a photo-multiplier tubes (PMTs), charge coupled devices (CCDs), time delay integration (TDI) camera, and the like. In addition, the output of the detector may be communicatively coupled to a controller 110, described in detail further herein.

In another embodiment, the inspection sub-system 102 includes one or more inspection channels. In another embodiment, at least a portion of the one or more inspection channels may direct illumination to one detector. In another embodiment, the one or more inspection channels may each direct illumination to a detector.

In one embodiment, the sample 104 includes one or more wafers. For example, the sample 104 may include, but is not limited to, one or more semiconductor wafers. As used through the present disclosure, the term "wafer" refers to a substrate formed of a semiconductor and/or non-semi-conductor material. For instance, a semiconductor or non-semiconductor material may include, but is not limited to, monocrystalline silicon, gallium arsenide, and indium phosphide.

In another embodiment, the sample stage 106 may include any appropriate mechanical and/or robotic assembly known in the art. In another embodiment, the controller 110 may actuate the sample stage 106. For example, the sample stage 106 may be configured by the controller 110 to actuate the sample 104 to a selected position or orientation. For instance, the sample stage 106 may include or may be mechanically coupled to one or more actuators, such as a motor or servo, configured to translate or rotate the sample 104 for positioning, focusing, and/or scanning in accordance with a selected inspection or metrology algorithm, several of which are known to the art.

In one embodiment, the controller 110 includes one or more processors 112 and a memory medium 114. In another embodiment, one or more sets of program instructions 116 are stored in memory medium 114. In another embodiment, the one or more processors 112 are configured to execute the sets of program instructions 116 to carry out one or more of the various steps described throughout the present disclosure.

In another embodiment, the controller 110 is configured to receive and/or acquire data or information from other systems or sub-systems (e.g., one or more sets of information from the inspection sub-system 102 or from any of the components of the inspection sub-system 102, or one or more user inputs received via the user interface 120) by a transmission medium that may include wireline and/or wireless portions. For example, the inspection sub-system 102 or any of the components of the inspection sub-system 102 may transmit one or more sets of information regarding the operation of the inspection sub-system 102 or any of the components of the inspection sub-system 102 to the controller 110. By way of another example, the inspection sub-system 102 may transmit one or more images of one or more inspected regions of the one or more samples 104 to the controller 110. For instance, the one or more images transmitted to the controller 110 may include, but are not limited to, one or more images of one or more inspection regions of the wafers 104.

In another embodiment, the controller 110 of the system 100 is configured to transmit data or information (e.g., the output of one or more procedures disclosed herein) to one or more systems or sub-systems (e.g., one or more commands to the inspection sub-system 102 or to any of the components of the inspection sub-system 102, the sample stage 106, or one or more outputs displayed on the user interface 120) by a transmission medium that may include wireline and/or wireless portions. In this regard, the transmission medium may serve as a data link between the controller 110 and other subsystems of the system 100. In another embodiment, the controller 110 is configured to send data to external systems via a transmission medium (e.g., network connection).

In another embodiment, the system 100 includes one or more encoders in the inspection sub-system 102, where the one or more encoders aggregate the one or more sets of information (e.g., the one or more images) prior to transmission of the one or more images to the controller 110. In another embodiment, the system 100 includes one or more decoders in the controller 110 to de-aggregate one or more sets of information (e.g., the one or more images) transmitted by the inspection sub-system 102. It is noted herein, however, that the controller 110 and the inspection sub-system 102 may additionally or alternatively include encoders or decoders, respectively.

In one example, a detector of the inspection sub-system 102 may be coupled to the controller 110 in any suitable manner (e.g., by one or more transmission media indicated by the dotted line shown in FIG. 1) such that the controller 110 may receive the output generated by the detector. By way of another example, if the inspection sub-system 102 includes more than one detector, the controller 110 may be coupled to the multiple detectors as described above. It is noted herein the controller 110 may be configured to detect one or more defects of the sample 104 using detection data collected and transmitted by the inspection sub-system 102, utilizing any method and/or algorithm known in the art to detect defects on the wafer. For example, the inspection sub-system 102 may be configured to accept instructions from another subsystem of the system 100 including, but not limited to, controller 110. Upon receiving the instructions from the controller 110, the inspection sub-system 102 may perform an inspection procedure at one or more locations (e.g., one or more regions to be inspected) of the sample 104 identified in the provided instructions (i.e., the inspection recipe), transmitting the results of the inspection procedure to the controller 110.

In one embodiment, the set of program instructions 116 are programmed to cause the one or more processors 112 to receive one or more images of three or more die of the wafer 104 from the inspection sub-system 102. In another embodiment, the set of program instructions 116 are programmed to cause the one or more processors 112 to determine a median intensity value of a set of pixel intensity values acquired from a same location on each of the three or more die. In another embodiment, the set of program instructions 116 are programmed to cause the one or more processors 112 to determine a difference intensity value for the set of pixel intensity values by comparing the median intensity value of the set of pixel intensity values to each pixel intensity value. In another embodiment, the set of program instructions 116 are programmed to cause the one or more processors 112 to group the pixel intensity values into an intensity bin based on the median intensity value of the set of pixel intensity values. In another embodiment, the set of program instructions 116 are programmed to cause the one or more processors 112 to generate an initial noise boundary based on a selected difference intensity value in the intensity bin. In another embodiment, the set of program instructions 116 are programmed to cause the one or more processors 112 to generate a final noise boundary by adjusting the initial noise boundary. In another embodiment, the set of program instructions 116 are programmed to cause the one or more processors 112 to generate a detection boundary by applying a threshold to the final noise boundary. In another embodiment, the set of program instructions 116 are programmed to cause the one or more processors 112 to classify one or more pixel intensity values outside the detection boundary as a defect.

In another embodiment, the set of program instructions 116 are programmed to generate one or more bright noise statistical values for each pixel on the one or more dies. In another embodiment, the set of program instructions 116 are programmed to generate one or more dark noise statistical values for each pixel on the one or more dies.

In another embodiment, the set of program instructions are programmed to generate one or more scatter plots. For example, the one or more scatter plots are configured to compare one or more pixel intensity values. By way of another example, the one or more scatter plots are configured to include one or more noise boundaries based on the one or more pixel intensity values.

In another embodiment, where the inspection sub-system 102 includes multiple inspection channels, the set of program instructions 116 are programmed to generate one or more reconstructed images by combining the one or more images acquired by the one or more channels of the inspection sub-system. In this embodiment, the set of program instructions 116 are programmed to classify a pixel as a defect only when the pixel is detected in a least a portion of the multiple inspection channels (i.e. is present in the reconstructed images). In this embodiment, the generating of one or more reconstructed images combines multiple inspection channel information of the difference of defect signal and noise boundary.

In one embodiment, the one or more processors 112 of controller 110 include any one or more processing elements known in the art. In this sense, the one or more processors 112 may include any microprocessor device configured to execute algorithms and/or instructions. For example, the one or more processors 112 may consist of a desktop computer, mainframe computer system, workstation, image computer, parallel processor, vehicle on-board computer, handheld computer (e.g., tablet, smartphone, or phablet), or other computer system (e.g., networked computer) configured to execute a program configured to operate the system 100, as described throughout the present disclosure. It should be recognized that the steps described throughout the present disclosure may be carried out by a single computer system or, alternatively, multiple computer systems. In general, the term "processor" may be broadly defined to encompass any device having one or more processing elements, which execute the program instructions 116 from a non-transitory memory medium (e.g., memory 114). Moreover, different subsystems of the system 100 (e.g., inspection sub-system 102 or user interface 120) may include processor or logic elements suitable for carrying out at least a portion of the steps described throughout the present disclosure. Therefore, the above description should not be interpreted as a limitation on the present disclosure but merely an illustration.

In one embodiment, the memory medium 114 of controller 110 includes any storage medium known in the art suitable for storing the program instructions 116 executable by the associated one or more processors 112. For example, the memory medium 114 may include a non-transitory memory medium. For instance, the memory medium 114 may include, but is not limited to, a read-only memory, a random access memory, a magnetic or optical memory device (e.g., disk), a magnetic tape, a solid state drive and the like. In another embodiment, it is noted herein that the memory 114 is configured to provide display information to a display device 122 and/or the output of the various steps described herein. It is further noted that memory 114 may be housed in a common controller housing with the one or more processors 112. In an alternative embodiment, the memory 114 may be located remotely with respect to the physical location of the processors 112 and controller 110. For instance, the one or more processors 112 of controller 110 may access a remote memory (e.g., server), accessible through a network (e.g., internet, intranet and the like). In another embodiment, the memory medium 114 stores the program instructions 116 for causing the one or more processors 112 to carry out the various steps described through the present disclosure.

In another embodiment, the user interface 120 is communicatively coupled to the one or more processors 112 of controller 110. In another embodiment, the user interface 120 includes a display device 122. In another embodiment, the user interface 120 includes a user input 124.

In one embodiment, the display device 122 includes any display device known in the art. For example, the display device may include, but is not limited to, a liquid crystal display (LCD). By way of another example, the display device may include, but is not limited to, an organic light-emitting diode (OLED) based display. By way of another example, the display device may include, but is not limited to, a CRT display. Those skilled in the art should recognize that a variety of display devices may be suitable for implementation in the present disclosure and the particular choice of display device may depend on a variety of factors, including, but not limited to, form factor, cost, and the like. In a general sense, any display device capable of integration with the user input device (e.g., touchscreen, bezel mounted interface, keyboard, mouse, trackpad, and the like) is suitable for implementation in the present disclosure.

In one embodiment, the user input device 124 includes any user input device known in the art. For example, user input device 124 may include, but is not limited to, a keyboard, a keypad, a touchscreen, a lever, a knob, a scroll wheel, a track ball, a switch, a dial, a sliding bar, a scroll bar, a slide, a handle, a touch pad, a paddle, a steering wheel, a joystick, a bezel input device or the like. In the case of a touchscreen interface, those skilled in the art should recognize that a large number of touchscreen interfaces may be suitable for implementation in the present disclosure. For instance, the display device 122 may be integrated with a touchscreen interface, such as, but not limited to, a capacitive touchscreen, a resistive touchscreen, a surface acoustic based touchscreen, an infrared based touchscreen, or the like. In a general sense, any touchscreen interface capable of integration with the display portion of a display device is suitable for implementation in the present disclosure. In another embodiment, the user input device 124 may include, but is not limited to, a bezel mounted interface.

The embodiments of the system 100 illustrated in FIG. 1 may be further configured as described herein. In addition, the system 100 may be configured to perform any other steps(s) of any of the system and method embodiment(s) described herein.

Figure 2:
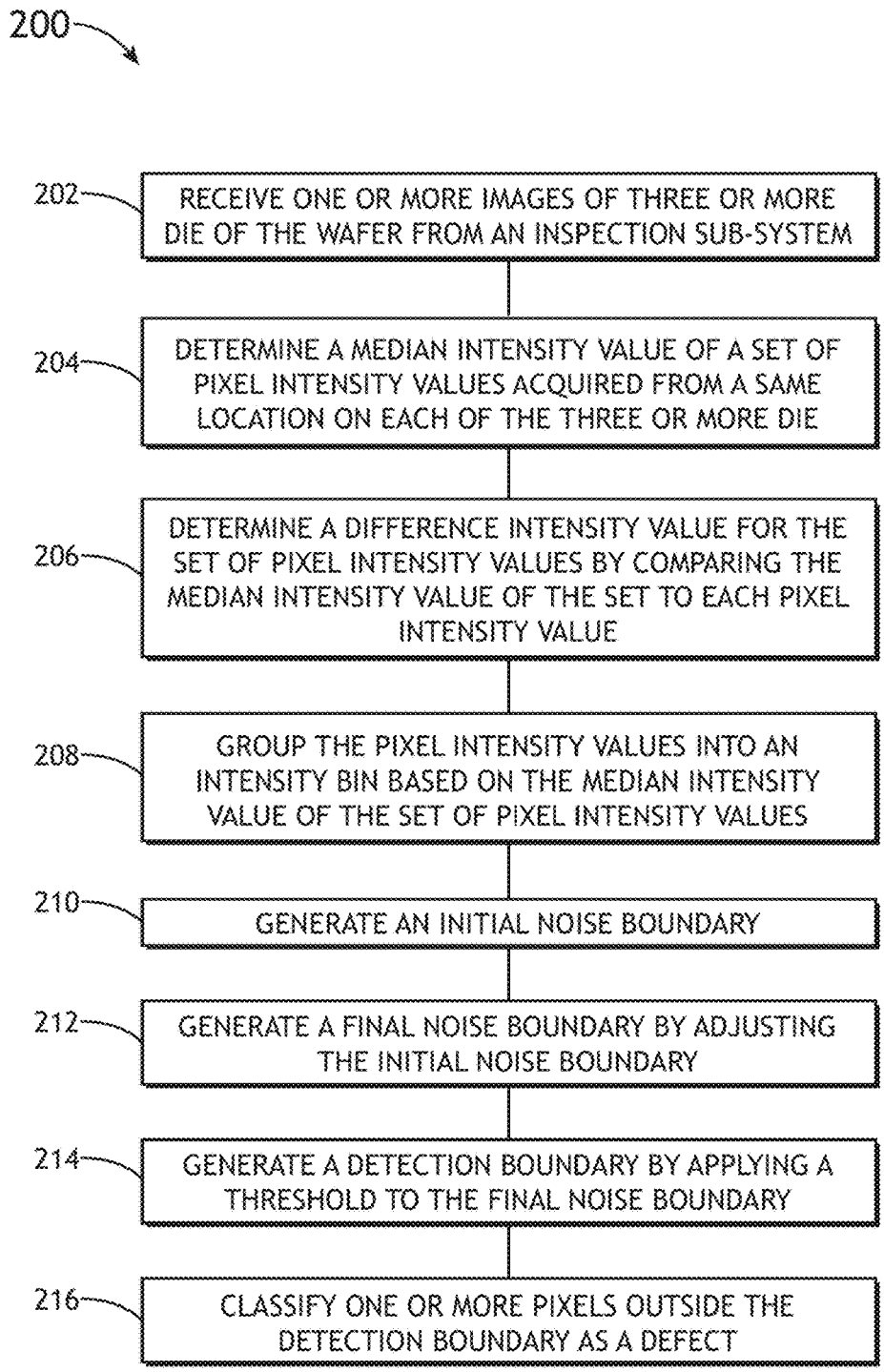
FIG. 2 illustrates a flow diagram depicting a method of locating one or more defects with a boundary thresholding procedure, in accordance with one or more embodiments of the present disclosure.

FIG. 2 illustrates a process flow diagram depicting a method 200 for inspecting a wafer with a noise boundary threshold procedure (NBT procedure 200). The method may also include any other step(s) that can be performed by the output acquisition subsystem and/or computer subsystem(s) or system(s) described herein. The steps may be performed by one or more computer systems, which may be configured according to any of the embodiments described herein. It is noted herein that the steps of method 200 may be implemented all or in part by the system 100. It is recognized, however, that the method 200 is not limited to the system 100 in that additional or alternative system-level embodiments may carry out all or part of the steps of method 200.

In one embodiment, the NBT procedure 200 includes separate noise statistics for each die of one or more dies. For example, the NBT procedure 200 does not assume noise is common to the one or more dies. In another embodiment, the NBT procedure 200 includes separate bright noise and dark noise statistics for each die of the one or more dies. For example, the NBT procedure 200 does not assume noise is common to both the bright defect and dark defect. It is noted herein the noise statistics and the bright noise and dark noise statistics may be calculated together or independently of one another. In another embodiment, the NBT procedure 200 does not implement a pre-defined (i.e. Gaussian) noise model.

In a step 202, one or more images of three or more dies of a wafer are received from an inspection sub-system 102. In another embodiment, the three or more dies include one or more pixel intensity values.

In another embodiment, the one or more pixel intensity values are at a same location (e.g., a set of x, y coordinates based on matching axes between the three or more dies). It is noted herein that one or more pixel intensity values at the same location are considered a set of pixel intensity values for purposes of the present disclosure. It is further noted herein there may be any number of sets of one or more pixel intensity values located at a same location on the three or more dies.

In another embodiment, the NBT procedure 200 is configured to receive the images that include a low number of defective pixels. It is noted herein, however, that the NBT 200 procedure may be applied to images with any number of defective pixels. In another embodiment, the NBT procedure 200 is configured to inspect noise that changes smoothly with pixel gray level (GL) changes. It is noted herein, however, that the NBT procedure 200 may inspect noise that changes unevenly with pixel GL changes. In another embodiment, the NBT procedure 200 may not detect one or more defects where the defective pixel difference intensity value is smaller than the difference intensity value of non-defective pixels with a similar GL. For example, the NBT procedure 200 may not detect defects buried under a noise floor.

In step 204, a median intensity value of a set of pixel intensity values acquired from a same location on each of the three or more die is determined. In one embodiment, three or more dies are preferable to perform statistical procedures, including the procedure of finding the median intensity value of each set of pixel intensity values. It is noted herein, however, there may be any number of dies, including two dies. In the case of two dies, either the higher or lower value of the intensity value is selected as the "median" intensity value. Therefore, the above description should not be interpreted as a limitation on the present disclosure but merely an illustration.

In step 206, a difference intensity value for the set of pixel intensity values is determined by comparing the median intensity value of the set to each pixel intensity value. In one embodiment, the difference intensity value is the median intensity value subtracted from each pixel intensity value. In another embodiment, the difference intensity value may be positive (i.e. the median intensity value is lower than the particular pixel intensity value). In another embodiment, the difference intensity value may be negative (i.e. the median intensity value is higher than the particular pixel intensity value).

Figure 3A:
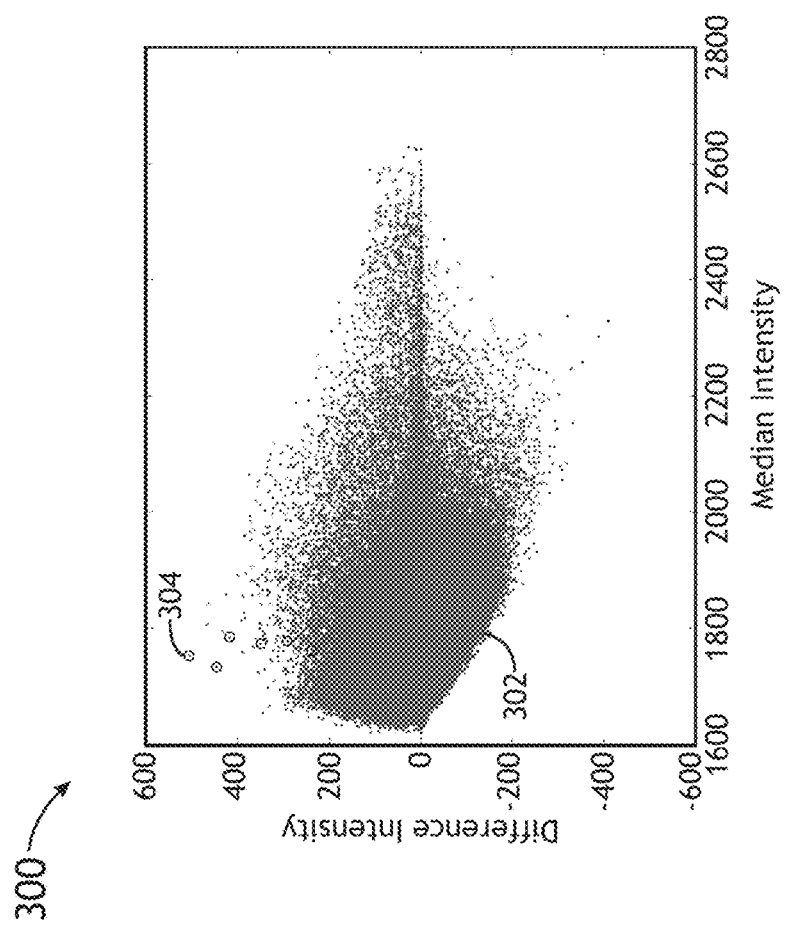
FIG. 3A illustrates graphical data including data for one or more pixel samples, in accordance with one or more embodiments of the present disclosure.

FIG. 3A illustrates graphical data 300 of a scatter plot, in accordance with one or more embodiments of the present disclosure. In one embodiment, the graphical data 300 plots the difference intensity value for each pixel intensity value of the set of pixel intensity values against the median intensity value of the set of pixel intensity values, as represented by T-median markers 302. In another embodiment, one or more potential defects are represented by DOI markers 304.

In step 208, the pixel intensity values are grouped into an intensity bin based on the median intensity value of the set of pixel intensity values. In one embodiment, the inspection sub-system 102 has a select intensity range. For example, the select intensity range may be [0 4095], or 4096 total points. It is noted herein, however, that the select intensity range may be any number of total points. In another embodiment, the intensity range is separated into one or more intensity bins. For example, the NBT procedure 200 may include a configurable number of intensity bins based on the application of the inspection system. For instance, the NBT procedure 200 may have 128 intensity bins. In another embodiment, the one or more intensity bins include a configurable number of pixel intensity values. For example, the NBT procedure 200 may include 32 pixel intensity values in each intensity bin. By way of another example, the NBT procedure 200 may include a smaller intensity bin size (e.g., 4 pixel intensity values in each bin) for better noise boundary determination where the pixel dynamic range is small (e.g., around 150 GL count). By way of another example, the NBT procedure 200 may have a larger intensity bin size to avoid the impact from local noise variation where the pixel dynamic range is larger. In another embodiment, the one or more intensity bins are defined by selectable median intensity value ranges. For example, the median intensity value range may be 0-100, 100-200, 200-300, and the like.

It is noted herein the NBT procedure 200 may include any number of intensity bins, any bin pixel containment size, or any range of median intensity value ranges. Therefore, the above description should not be interpreted as a limitation on the present disclosure but merely an illustration.

Figure 3B:
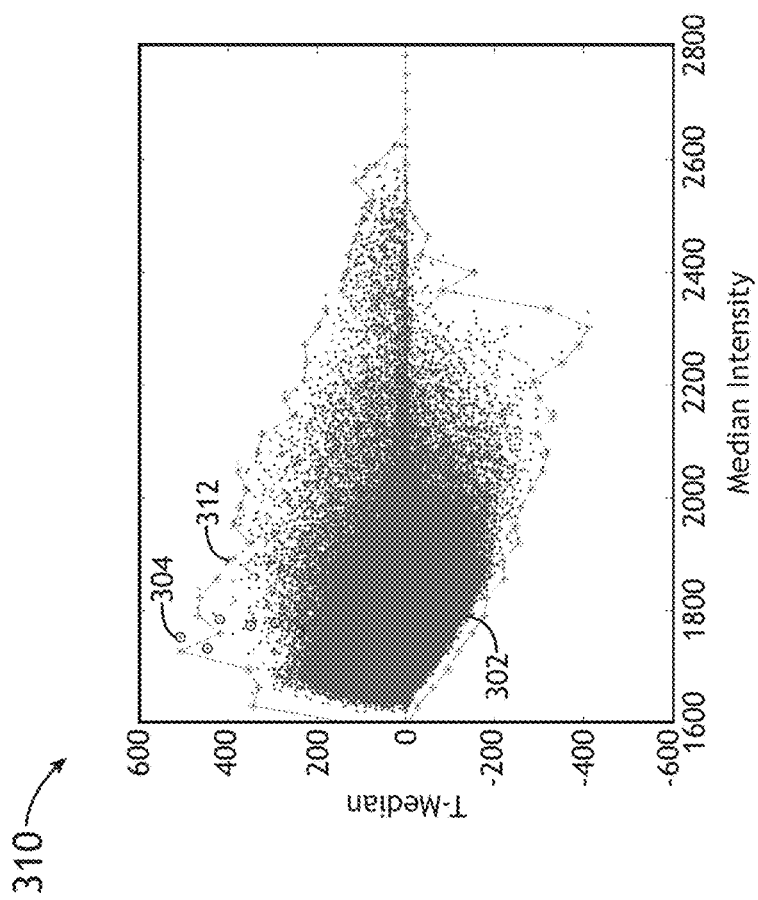
FIG. 3B illustrates graphical data including one or more initial noise boundaries, in accordance with one or more embodiments of the present disclosure.

In step 210, the NBT procedure 200 generates an initial noise boundary 312 based on a selected difference intensity value in the one or more intensity bins. For example, the selected difference intensity value may be the largest positive difference intensity value. By way of another example, the selected difference intensity value may be the smallest negative difference intensity value in the one or more intensity bins. FIG. 3B illustrates graphical data 310 of a scatter plot including the initial noise boundary 312, in accordance with one or more embodiments of the present disclosure.

Figure 4A:
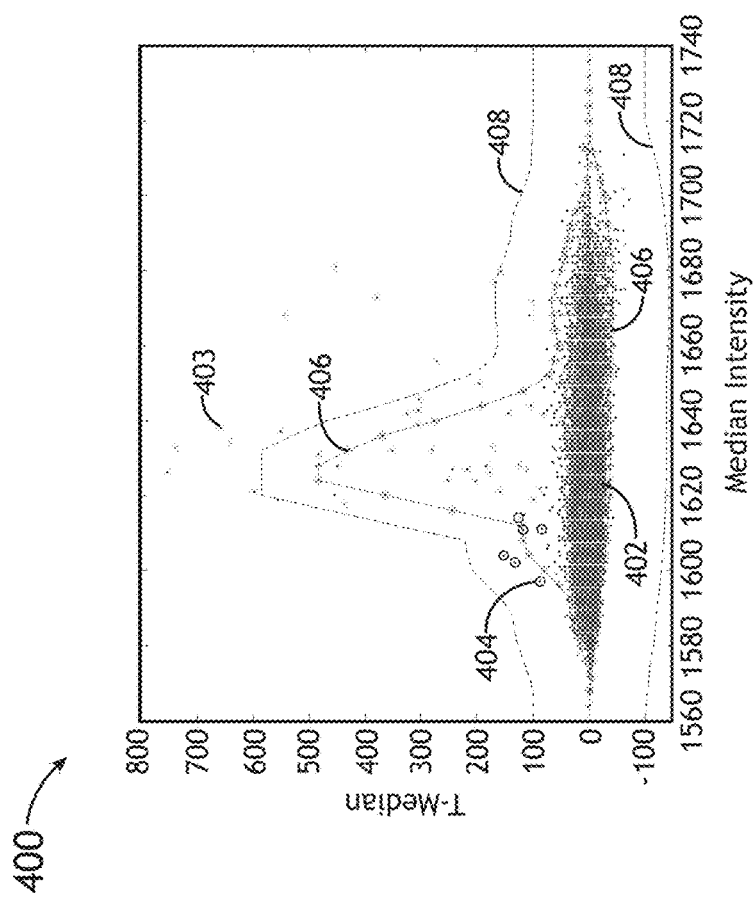
FIG. 4A illustrates graphical data including one or more noise boundaries, in accordance with one or more embodiments of the present disclosure.
Figure 4B:
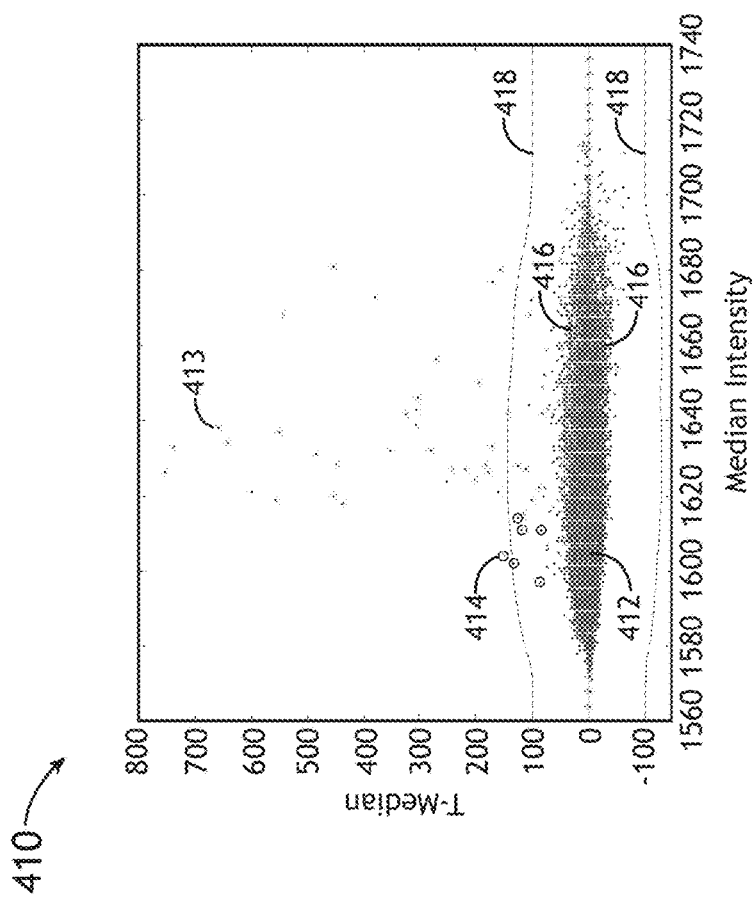
FIG. 4B illustrates graphical data including one or more noise boundaries, in accordance with one or more embodiments of the present disclosure.

In another embodiment, the selected difference intensity value may be the Nth-largest positive (or Nth-smallest negative) intensity value, where N is a selectable and configurable parameter (e.g., 8 or 10). FIG. 4A illustrates graphical data 400 of a scatter plot, in accordance with one or more embodiments of the present disclosure. In one embodiment, the graphical data 400 includes one or more T-median values 402, one or more outlier T-median values 403, one or more DOI 404, one or more noise boundaries 406, and one or more detection boundaries 408. As illustrated in FIG. 4A, selecting the largest positive difference intensity results in a skewed noise boundary 406 and detection boundary 408 due the one or more outlier T-median values 403, meaning the selecting of the largest positive difference intensity value would result in one or more missed DOI 404. FIG. 4B illustrates graphical data 410 of a scatter plot, in accordance with one or more embodiments of the present disclosure. In one embodiment, the graphical data 410 includes one or more T-median values 412, one or more outlier T-median values 413, one or more DOI 414, one or more noise boundaries 416, and one or more detection boundaries 418. As illustrated in FIG. 4B selecting the Nth-largest positive difference intensity value results in a noise boundary 416 and detection boundary 418 that is able to observe the one or more DOI 414. It is noted application of the Nth parameter may be a more precise method of tracking defects than selecting the largest positive (or smallest negative) difference intensity, and further may be the only method when the defect is above a certain size (i.e. is a scratch or full missing structure) where a large number of pixel intensity values corresponding to defective pixels exist.

It is noted herein that the NBT procedure 200 may select multiple difference intensity values. For example, the NBT procedure 200 may select the largest positive difference intensity value and the $2^{nd}$-largest positive difference intensity value. For instance, the NBT procedure 200 may elect the $2^{nd}$-largest positive difference intensity value for the selected difference intensity value of the intensity bin. By way of another example, the NBT procedure 200 may select any number of difference intensity values, and additionally may elect to keep any of the difference intensity values as the selected difference intensity value of the intensity bin.

In another embodiment, although not shown, a bright noise boundary is generated independently of the initial noise boundary 312. In another embodiment, although not shown, a dark noise boundary is generated independently of the initial noise boundary 312.

Figure 3C:
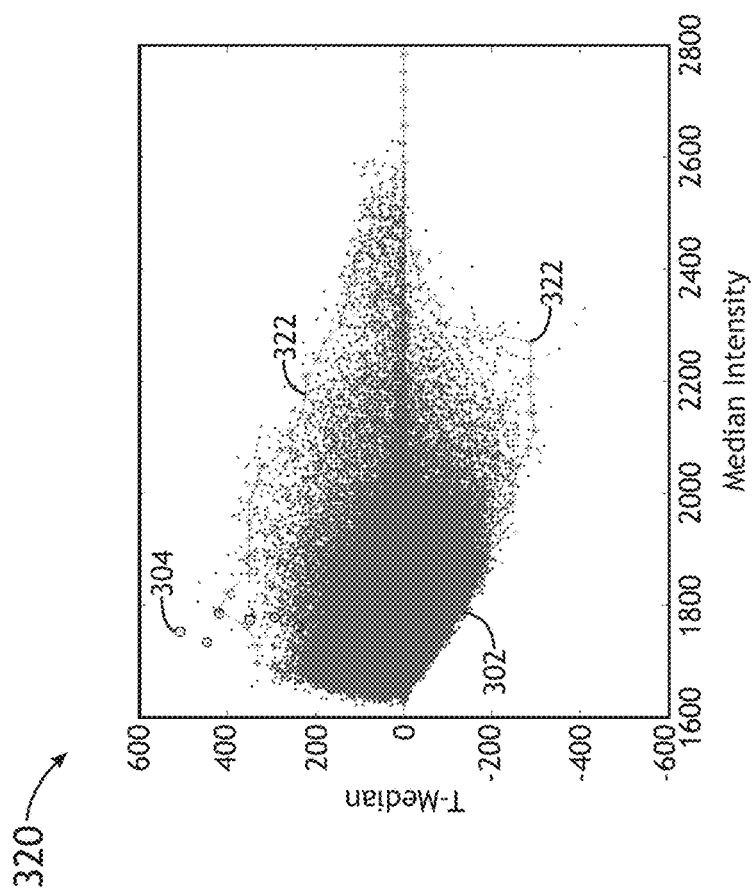
FIG. 3C illustrates graphical data including one or more noise boundaries, in accordance with one or more embodiments of the present disclosure.

In step 212, a final noise boundary is generated by adjusting the initial noise boundary 312. In one embodiment, an adjacent minimum intensity bin value is selected. In another embodiment, a minimum intensity value for each of the one or more intensity bins is determined. In another embodiment, a first adjusted noise boundary is generated from the initial noise boundary 312. FIG. 3C illustrates graphical data 320 of a scatter plot including the initial noise boundary 322, in accordance with one or more embodiments of the present disclosure.

For example, an adjacent minimum intensity bin value of 5 may be selected, meaning a bin and its 2 left and 2 right adjacent bins. By way of another example, the initial noise value of the bin is adjusted to the minimum of the 5 selected adjacent bins, from which a first adjusted noise boundary is generated.

In another embodiment, an adjacent maximum intensity bin value is selected. In another embodiment, a maximum intensity value for each of the one or more intensity bins from the first adjusted noise boundary is determined. In another embodiment, a second adjusted noise boundary is generated from the first adjusted noise boundary.

For example, the adjacent maximum intensity bin value of 5 may first be selected, meaning a bin and its 2 left and 2 right adjacent bins. By way of another example, the first adjusted noise value of the bin is adjusted to maximum of the 5 selected adjacent bins, from which a second adjusted noise boundary is generated.

It is noted herein the order of adjacent minimum and adjacent maximum procedures is dependent on whether the initial noise boundary is positive in nature or negative in nature. For example, the minimum and maximum procedures may be performed in the order listed on the initial noise boundary based on the largest positive difference intensity value. In this example, the adjacent minimum intensity bin value is found to remove defect contributions from the initial noise boundary, and the adjacent maximum intensity bin value is found to raise the value of non-defective bins improperly lowered. By way of another example, the minimum and maximum procedures may be performed in reverse order from that listed on the initial noise boundary based on the smallest negative difference intensity value. In this example, the adjacent maximum intensity bin value is found to remove defect contributions from the initial noise boundary, and the adjacent minimum intensity bin value is found to lower the value of non-defective bins improperly raised.

Figure 3D:
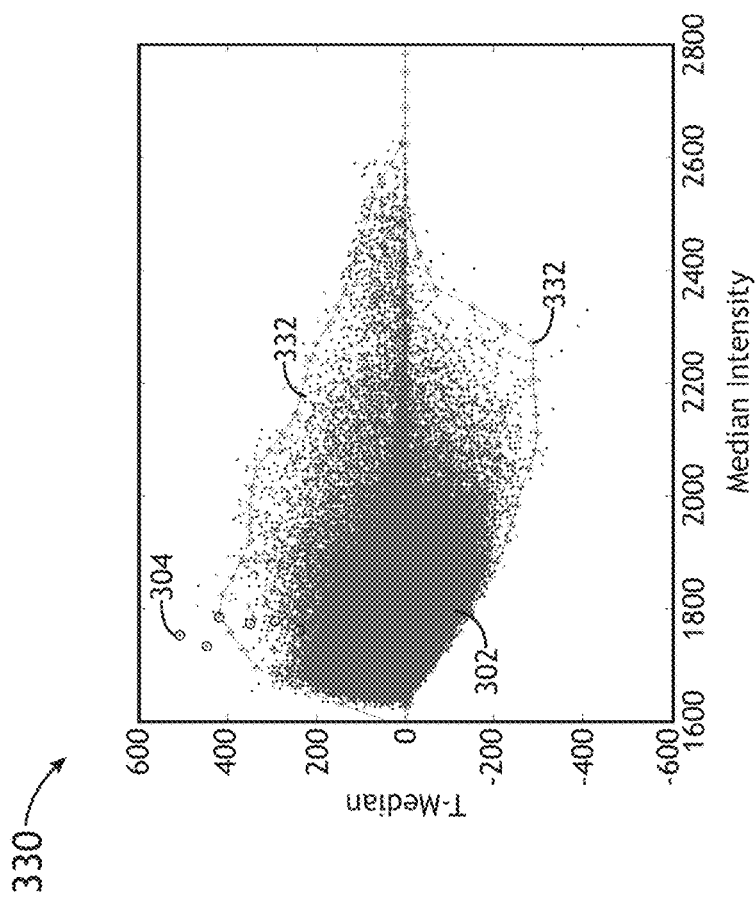
FIG. 3D illustrates graphical data including one or more noise boundaries, in accordance with one or more embodiments of the present disclosure.

In an additional step, the second adjusted noise boundary is smoothed. In one embodiment, an adjacent mean intensity bin value is selected. In another embodiment, a mean intensity value for each of the one or more intensity bins is determined. For example, the mean difference intensity value may be determined by averaging the second adjusted noise boundary value of each intensity bin. In another embodiment, a third adjusted noise boundary is generated from the second adjusted noise boundary. It is noted herein the third adjusted noise boundary may additionally be considered a smoothed noise boundary, for purposes of the present disclosure. FIG. 3D illustrates graphical data 330 of a scatter plot including the third adjusted noise boundary 332, in accordance with one or more embodiments of the present disclosure.

Figure 5A:
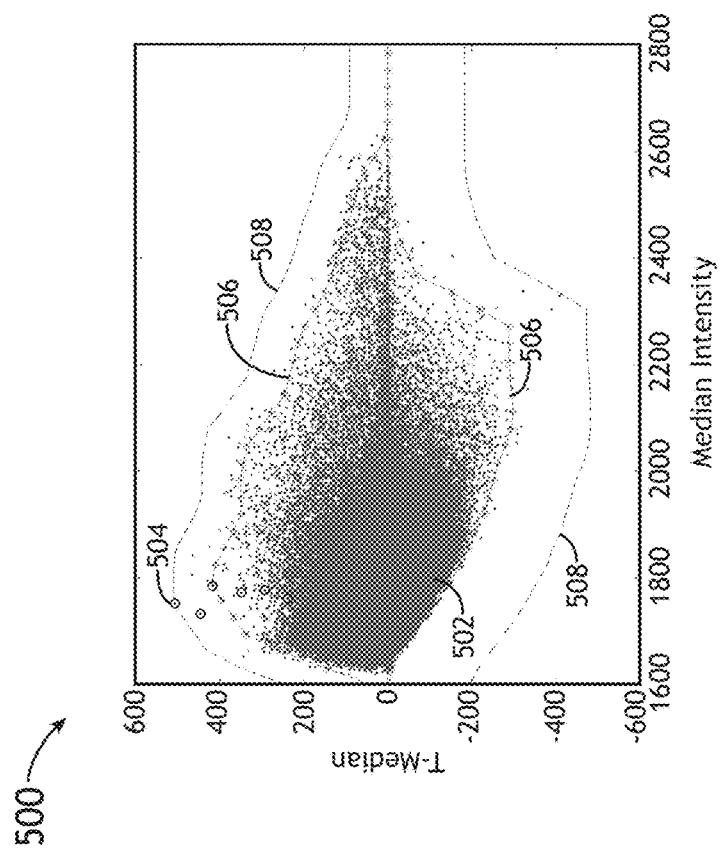
FIG. 5A illustrates graphical data including one or more noise boundaries, in accordance with one or more embodiments of the present disclosure.

In an additional step, the third adjusted noise boundary 332 is interpolated to generate a final noise boundary. For example, in the case of a 128-bin system, the 128-bin smoothed boundary is interpolated to include 4096 points to generate the final noise boundary. For example, FIG. 5A illustrates graphical data 500 of a scatter plot including the interpolated noise boundary 506, in accordance with one or more embodiments of the present disclosure.

It is noted herein that one or more of the sub-steps of step 212 may be removed from the NBT procedure 200. For example, although embodiments of the present disclosure are directed to generating a first adjusted noise boundary, a second adjusted noise boundary, and a third adjusted noise boundary, it is noted herein that fewer than three adjusted noise boundaries may be generated (i.e. a noise boundary based only on the minimum or maximum adjacent intensity bin value). It is further noted herein that at least a fourth adjusted noise boundary may be generated prior to a final noise boundary, discussed in detail further herein.

Therefore, the above description should not be interpreted as a limitation on the present disclosure but merely an illustration.

In step 214, a detection boundary is generated by applying (i.e. adding or multiplying) a threshold to the final noise boundary. In one embodiment, the threshold is a configurable parameter. For example, the threshold may be configured by the inspection sub-system 102. By way of another example, the threshold may be configured by a user. By way of another example, the threshold may be configured by the controller 110. FIG. 5A illustrates graphical data 500 of a scatter plot including the detection or threshold noise boundary 508, in accordance with one or more embodiments of the present disclosure.

In step 216, one or more pixels outside the detection boundary are classified as a defect. In one embodiment, the one or more pixel intensity values outside the detection boundary correspond to one or more pixels in the one or more images. In another embodiment, outside refers to pixel intensity values above the largest positive detection boundary. In another embodiment, outside refers to pixel intensity values below the smallest negative detection boundary.

It is noted herein the NBT procedure 200 is not limited to a generating a single instance of the initial noise boundary 312, the adjusted noise boundaries 322 and 332, the final noise boundary 506, or the detection or threshold boundary 508. For example, the NBT procedure 200 may generate at least two of each boundary.

Figure 5B:
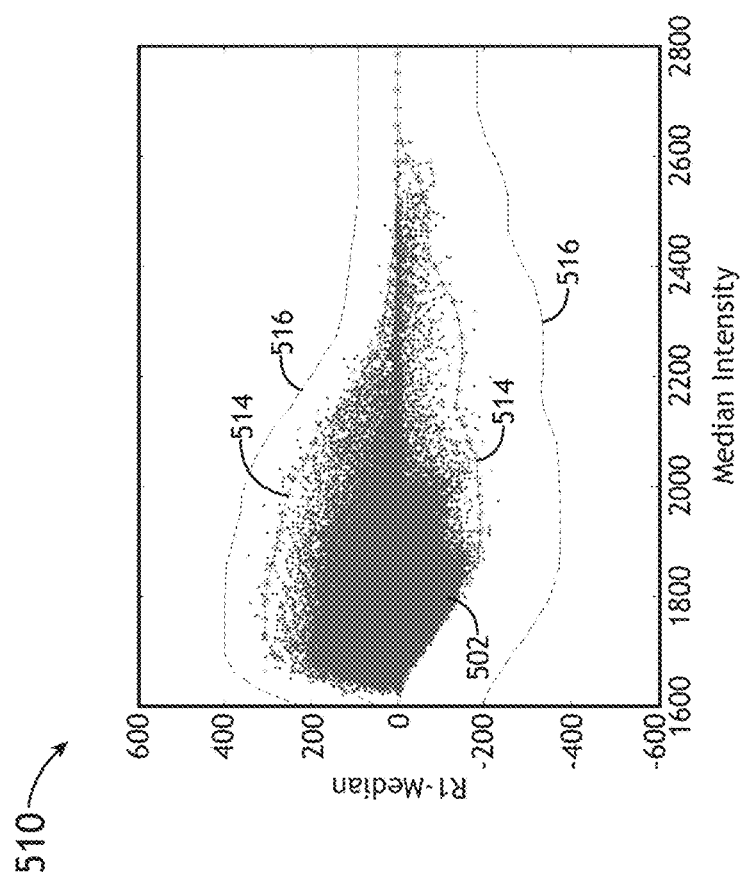
FIG. 5B illustrates graphical data including one or more noise boundaries, in accordance with one or more embodiments of the present disclosure.
Figure 5C:
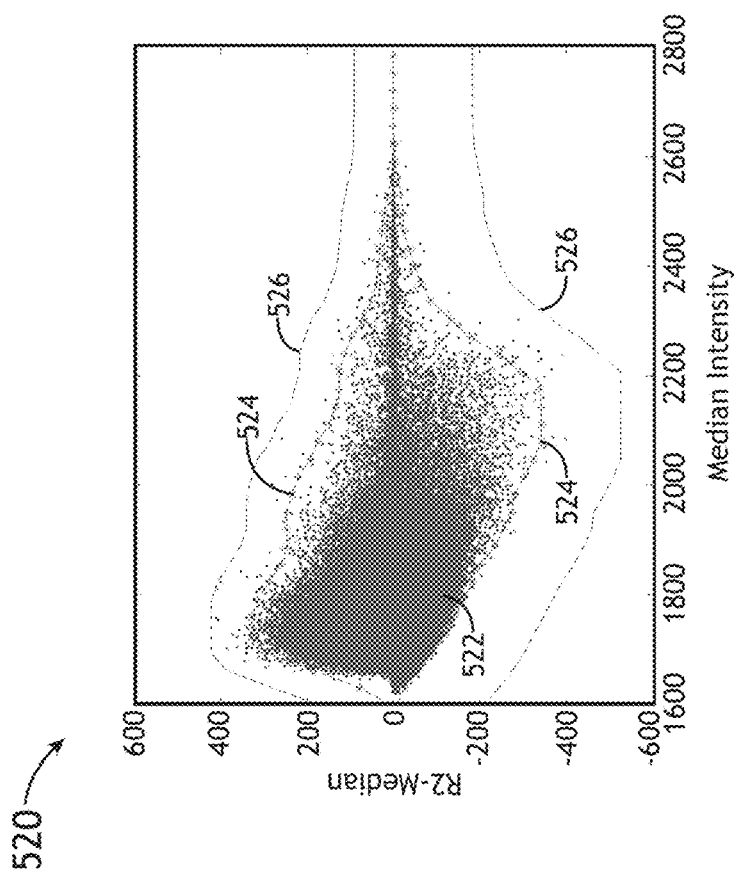
FIG. 5C illustrates graphical data including one or more noise boundaries, in accordance with one or more embodiments of the present disclosure.

FIG. 5A-5C illustrate a target die and a set of reference dies on one or more wafers, in accordance with one or more embodiments of the present disclosure. FIG. 5A illustrates graphical data 500 including one or more noise boundaries, in accordance with one or more embodiments of the present disclosure. In one embodiment, the graphical data 500 includes one or more T-median values 502, one or more DOI 504, the one or more final noise boundaries 506, and the one or more detection or threshold boundaries 508. FIG. 5B illustrates graphical data 510 including one or more noise boundaries, in accordance with one or more embodiments of the present disclosure. In one embodiment, the graphical data 510 includes one or more T-median values 512, one or more final noise boundaries 514, and one or more detection or threshold boundaries 516. FIG. 5C illustrates graphical data 500 including one or more noise boundaries, in accordance with one or more embodiments of the present disclosure. In one embodiment, the graphical data 520 includes one or more T-median values 522, one or more final noise boundaries 524, and one or more detection or threshold boundaries 526.

As illustrated in FIGS. 5A through 5C, the noise distribution in each die are different. Additionally, as illustrated in FIGS. 5A through 5C, the noise distribution in each die are different for bright and dark noise. Further, as illustrated in FIGS. 5A through 5C, the detection boundaries 508, 516, 526 each follow the corresponding final noise boundaries 506, 514, 524, respectively.

It is noted herein the one or more scatter plots represented in the graphical data of FIGS. 3A-5C are conceptual illustrations, as generating a 2D scatter plot over the entire histogram (e.g., as implemented by a MDAT BBP procedure) would be prohibitive to wafer inspection and review speed in terms of memory and computation power. In one embodiment, the NBT procedure 200 stores any of the initial noise boundary 312; the adjusted noise boundaries 322, 332; the final noise boundaries 506, 514, 524; the detection or threshold boundaries 508, 516, 526; bright noise boundaries; and/or dark noise boundaries. In another embodiment, storing the boundaries allows the NBT procedure 200 to perform fewer computational operations than the FAST procedure. For example, the NBT procedure 200 requires the computation power to compare 1 value and assign 1 value. By way of another example, the FAST procedure requires the computation power to determine the sum of intensities and the square of the sum of intensities. It is further noted herein, however, that the NBT procedure 200 may generate one or more scatter plots and display them on the display 122 of the user interface 120. Therefore, the above description should not be interpreted as a limitation on the present disclosure but merely an illustration.

It is noted herein the results of applying the NBT procedure 200 to the results of the inspection or review of sample 104 may be used by the controller 110 (or another controller, a user, or a remote server) to provide feedback or feedforward information to one or more processing tools of a semiconductor device fabrication line. In this regard, one or more results observed or measured by the system 100 may be used to adjust process conditions at previous stages (feedback) or subsequent stages (feedforward) of the semiconductor device fabrication line.

It is further noted herein the NBT procedure 200 may be implemented into existing wafer inspection procedures as an independent set-up. For example, the NBT procedure 200 may run in parallel with other wafer inspection procedures such as FAST and CF2. By way of another example, the NBT procedure 200 has a new set of wafer inspection recipe parameters, but may adopt the same data flow as other wafer inspection procedures. By way of another example, the NBT procedure 200 may generate a new set of defect attributes and add the attributes to a result buffer. By way of another example, the detection result of the NBT procedure 200 may be merged with results from other wafer inspection procedures into a final result.

All of the methods described herein may include storing results of one or more steps of the method embodiments in a storage medium. The results may include any of the results described herein and may be stored in any manner known in the art. The storage medium may include any storage medium described herein or any other suitable storage medium known in the art. After the results have been stored, the results can be accessed in the storage medium and used by any of the method or system embodiments described herein, formatted for display to a user, used by another software module, method, or system, etc. Furthermore, the results may be stored "permanently," "semi-permanently," temporarily, or for some period of time. For example, the storage medium may be random access memory (RAM), and the results may not necessarily persist indefinitely in the storage medium.

Those having skill in the art will recognize that the state of the art has progressed to the point where there is little distinction left between hardware and software implementations of aspects of systems; the use of hardware or software is generally (but not always, in that in certain contexts the choice between hardware and software can become significant) a design choice representing cost vs. efficiency tradeoffs. Those having skill in the art will appreciate that there are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Those skilled in the art will recognize that optical aspects of implementations will typically employ optically-oriented hardware, software, and or firmware.

Those skilled in the art will recognize that it is common within the art to describe devices and/or processes in the fashion set forth herein, and thereafter use engineering practices to integrate such described devices and/or processes into data processing systems. That is, at least a portion of the devices and/or processes described herein can be integrated into a data processing system via a reasonable amount of experimentation. Those having skill in the art will recognize that a typical data processing system generally includes one or more of a system unit housing, a video display device, a memory such as volatile and non-volatile memory, processors such as microprocessors and digital signal processors, computational entities such as operating systems, drivers, graphical user interfaces, and applications programs, one or more interaction devices, such as a touch pad or screen, and/or control systems including feedback loops and control motors (e.g., feedback for sensing position and/or velocity; control motors for moving and/or adjusting components and/or quantities). A typical data processing system may be implemented utilizing any suitable commercially available components, such as those typically found in data computing/communication and/or network computing/communication systems.

It is believed that the present disclosure and many of its attendant advantages will be understood by the foregoing description, and it will be apparent that various changes may be made in the form, construction and arrangement of the components without departing from the disclosed subject matter or without sacrificing all of its material advantages. The form described is merely explanatory, and it is the intention of the following claims to encompass and include such changes.

Although particular embodiments of this invention have been illustrated, it is apparent that various modifications and embodiments of the invention may be made by those skilled in the art without departing from the scope and spirit of the foregoing disclosure. Accordingly, the scope of the invention should be limited only by the claims appended hereto.

What is claimed:
1. A wafer inspection system, comprising:
an inspection sub-system;
a stage configured to secure a wafer; and
a controller communicatively coupled to the inspection sub-system, wherein the controller includes one or more processors configured to execute a set of program instructions stored in memory, wherein the program instructions are configured to cause the one or more processors to:
receive one or more images of three or more dies of the wafer from the inspection sub-system;
identify a plurality of sets of pixel intensity values, wherein a particular set of pixel intensity values of the plurality of sets of pixel intensity values includes three or more pixel intensity values associated with a particular location common to the three or more dies;
for at least one selected set of pixel intensity values of the plurality of sets of pixel intensity values:
determine a median intensity value for the selected set of pixel intensity values;
determine a difference intensity value for each of the three or more pixel intensity values of the selected set of pixel intensity values by comparing the median intensity value of the selected set of pixel intensity values to each of the three or more pixel intensity values in the selected set of pixel intensity values; and
group the selected set of pixel intensity values into a selected intensity bin of a plurality of intensity bins based on the median intensity value of the selected set of pixel intensity values;

for at least one selected intensity bin of the plurality of intensity bins:
generate a positive noise boundary for the selected intensity bin including an Nth largest positive difference intensity value in the selected intensity bin, wherein N is a selected integer;
generate a positive detection boundary by applying a threshold to the positive noise boundary; and
classify any pixel intensity values in any of the plurality of intensity bins higher than the positive detection boundary as a defect.

2. The system in claim 1, wherein the selected difference intensity value includes:
a largest positive difference intensity value in the intensity bin, a smallest negative difference intensity value in the intensity bin, or a selectable difference intensity value below the largest positive difference intensity value or above the smallest negative difference intensity value.

3. The system in claim 1, wherein the program instructions are configured to cause the one or more processors to:
select an adjacent maximum intensity bin value;
group one or more intensity bins based on the adjacent maximum intensity bin value;
determine a maximum intensity value for the one or more intensity bins by comparing the intensity value of each intensity bin;
generate a first adjusted noise boundary from an initial noise boundary by increasing the intensity value of the one or more intensity bins to the maximum intensity value;
select an adjacent minimum intensity bin value;
group one or more intensity bins based on the adjacent minimum intensity bin value;
determine a minimum intensity value for the one or more intensity bins by comparing the intensity value of each intensity bin; and
generate a second adjusted noise boundary from the first adjusted noise boundary by reducing the intensity value of the one or more intensity bins to the minimum intensity value.

4. The system in claim 3, wherein the program instructions are further configured to cause the one or more processors to:
select an adjacent mean intensity bin value;
group one or more intensity bins based on the adjacent mean intensity bin value;
determine a mean intensity value for the one or more intensity bins by comparing the second adjusted noise boundary value of each intensity bin; and
generate a third adjusted noise boundary from the second adjusted noise boundary by setting the intensity value of the one or more intensity bins to the mean intensity value.

5. The system in claim 1, wherein the program instructions are further configured to cause the one or more processors to:
interpolate the positive noise boundary to a selected number of bins prior to generating the positive detection boundary.

6. The system in claim 1, wherein the program instructions are further configured to cause the one or more processors to:
determine a bright noise boundary for each of the three or more dies.

7. The system in claim 1, wherein the program instructions are further configured to cause the one or more processors to:
determine a dark noise boundary for each of the three or more dies.

8. The system in claim 1, wherein the inspection sub-system comprises one or more imaging channels, wherein the one or more imaging channels acquire the one or more images of the three or more dies of the wafer.

9. The system in claim 1, wherein the program instructions are further configured to cause the one or more processors to:
receive the one or more images of the three or more dies of the wafer acquired by the one or more channels of the inspection sub-system;
generate one or more reconstructed images by combining the one or more images acquired by the one or more channels of the inspection sub-system; and
classify one or more pixels outside the detection boundary in the one or more reconstructed images as a defect.

10. The system in claim 1, wherein the set of program instructions are further configured to cause the one or more processors to:
adjust a positive noise boundary value for the selected intensity bin, prior to generating the positive detection boundary, to an average of the positive noise boundary values within a selected number of intensity bins adjacent to the selected intensity bin.

11. The system in claim 1, wherein the positive noise boundary is an initial positive noise boundary, wherein the set of program instructions are further configured to cause the one or more processors to:
generate an adjusted positive noise boundary for the selected intensity bin, the adjusted positive noise boundary including a minimum value of the initial positive noise boundary within a selected number of intensity bins adjacent to the selected intensity bin; and
generate a final positive noise boundary for the selected intensity bin, the final positive noise boundary including a maximum value of the adjusted positive noise boundary within a selected number of adjacent intensity bins of the plurality of intensity bins, wherein generating the positive detection boundary comprises:
generating the positive detection boundary by applying the threshold to the final positive noise boundary.

12. The system in claim 1, wherein the set of program instructions are further configured to cause the one or more processors to:
for at least one selected intensity bin of the plurality of intensity bins:
generate a negative noise boundary for the selected intensity bin including an Mth smallest negative difference intensity value in the selected intensity bin, wherein M is a selected integer;
generate a negative detection boundary by applying a threshold to the negative noise boundary; and
classify any pixel intensity values in any of the plurality of intensity bins lower than the negative detection boundary as a defect.

13. The system in claim 12, wherein the set of program instructions are further configured to cause the one or more processors to:
interpolate the negative noise boundary to a selected number of bins prior to generating the negative detection boundary.

14. The system in claim 12, wherein the negative noise boundary is an initial negative noise boundary, wherein the set of program instructions are further configured to cause the one or more processors to:
generate an adjusted negative noise boundary for the selected intensity bin, the adjusted negative noise boundary including a maximum value of the initial negative noise boundary within a selected number of intensity bins adjacent to the selected intensity bin; and
generate a final negative noise boundary for the selected intensity bin, the final negative noise boundary including a minimum value of the adjusted negative noise boundary within a selected number of adjacent intensity bins of the plurality of intensity bins, wherein generating the negative detection boundary comprises:
generating the negative detection boundary by applying the threshold to the final negative noise boundary.

15. A method, comprising:
receiving one or more images of three or more dies of a wafer from an inspection sub-system;
identifying a plurality of sets of pixel intensity values, wherein a particular set of pixel intensity values of the plurality of sets of pixel intensity values includes three or more pixel intensity values associated with a particular location common to the three or more dies;
for at least one selected set of pixel intensity values of the plurality of sets of pixel intensity values:
determining a median intensity value for the selected set of pixel intensity values;
determining a difference intensity value for each of the three or more pixel intensity values of the selected set of pixel intensity values by comparing the median intensity value of the selected set of pixel intensity values to each of the three or more pixel intensity values in the selected set of pixel intensity values; and
grouping the selected set of pixel intensity values into a selected intensity bin of a plurality of intensity bins based on the median intensity value of the selected set of pixel intensity values;
for at least one selected intensity bin of the plurality of intensity bins:
generating a positive noise boundary for the selected intensity bin including an Nth largest positive difference value in the selected intensity bin, wherein N is a selected integer;
generating a positive detection boundary by applying a threshold to the final positive noise boundary; and
classifying any pixel intensity values in any of the plurality of intensity bins higher than the positive detection boundary as a defect.

16. The method in claim 15, wherein the selected difference intensity value includes:
a largest positive difference intensity value in the intensity bin, a smallest negative difference intensity value in the intensity bin, or a selectable difference intensity value below the largest positive difference intensity value or above the smallest negative difference intensity value.

17. The method in claim 15, further comprising:
selecting an adjacent maximum intensity bin value; grouping one or more intensity bins based on the adjacent maximum intensity bin value;
determining a maximum intensity value for the one or more intensity bins by comparing the intensity value of each intensity bin;
generating a first adjusted noise boundary from the initial noise boundary by increasing the intensity value of the one or more intensity bins to the maximum intensity value;
selecting an adjacent minimum intensity bin value; grouping one or more intensity bins based on the adjacent minimum intensity bin value;
determining a minimum intensity value for the one or more intensity bins by comparing the intensity value of each intensity bin; and
generating a second adjusted noise boundary from the first adjusted noise boundary by reducing the intensity value of the one or more intensity bins to the minimum intensity value.

18. The method in claim 17, further comprising:
selecting an adjacent mean intensity bin value;
grouping one or more intensity bins based on the adjacent mean intensity bin value;
determining a mean intensity value for the one or more intensity bins by comparing the second adjusted noise boundary value of each intensity bin; and
generating a third adjusted noise boundary from the second adjusted noise boundary by setting the intensity value of the one or more intensity bins to the mean intensity value.

19. The method in claim 15, further comprising:
interpolating the positive noise boundary to a selected number of bins prior to generating the positive detection boundary.

20. The method in claim 15, further comprising:
determining a bright noise boundary for each of the three or more dies.

21. The method in claim 15, further comprising:
determining a dark noise boundary for each of the three or more dies.

22. The method in claim 15, wherein the inspection sub-system comprises one or more imaging channels, wherein the one or more imaging channels acquire the one or more images of the three or more dies of the wafer.

23. The method in claim 15, further comprising:
receiving the one or more images of the three or more dies of the wafer acquired by the one or more channels of the inspection sub-system;
generating one or more reconstructed images by combining the one or more images acquired by the one or more channels of the inspection sub-system; and
classifying one or more pixels outside the detection boundary in the one or more reconstructed images as a defect.

24. The method in claim 15, further comprising:
for at least one selected intensity bin of the plurality of intensity bins:
generating a negative noise boundary for the selected intensity bin including an Mth smallest negative difference intensity value in the selected intensity bin, wherein M is a selected integer;
generating a negative detection boundary by applying a threshold to the negative noise boundary; and
classifying any pixel intensity values in any of the plurality of intensity bins lower than the negative detection boundary as a defect.

* * * * *